(12) United States Patent
Gibson

(10) Patent No.: US 6,878,195 B2
(45) Date of Patent: Apr. 12, 2005

(54) AIR TREATMENT APPARATUS

(75) Inventor: Phillip George Gibson, Kent (GB)

(73) Assignee: Vent Master (Europe) Ltd., Rochester (GB)

( * ) Notice: Subject to any disclaimer, the term of this patent is extended or adjusted under 35 U.S.C. 154(b) by 0 days.

(21) Appl. No.: 10/753,092

(22) Filed: Jan. 7, 2004

(65) Prior Publication Data

US 2004/0211321 A1 Oct. 28, 2004

Related U.S. Application Data

(63) Continuation-in-part of application No. 10/182,915, filed on Oct. 1, 2002, and a continuation-in-part of application No. PCT/GB01/00456, filed on Feb. 5, 2001.

(30) Foreign Application Priority Data

Feb. 4, 2000 (GB) .............................................. 0002679

(51) Int. Cl.⁷ ................................................ A61L 9/20
(52) U.S. Cl. ...................... 96/224; 55/DIG. 36; 95/19; 95/22; 96/400; 422/24; 422/121
(58) Field of Search .......................... 96/224, 16, 400; 422/24, 121; 95/19–22; 55/DIG. 36, DIG. 18; 454/49, 56

(56) References Cited

U.S. PATENT DOCUMENTS

| | | | | |
|---|---|---|---|---|
| 3,745,750 A | * | 7/1973 | Arff ............................... | 96/16 |
| 3,846,072 A | * | 11/1974 | Patterson ..................... | 96/222 |
| 4,210,429 A | * | 7/1980 | Golstein ....................... | 96/142 |
| 5,042,457 A | * | 8/1991 | Gallagher ................ | 126/299 E |
| 5,112,370 A | * | 5/1992 | Gazzano ..................... | 422/121 |
| 5,152,814 A | * | 10/1992 | Nelson .......................... | 96/224 |
| 5,523,057 A | * | 6/1996 | Mazzilli ....................... | 422/121 |
| 5,704,955 A | * | 1/1998 | Giles .............................. | 96/26 |
| 5,718,219 A | * | 2/1998 | Boudreault ............. | 126/299 E |
| 5,891,399 A | * | 4/1999 | Owesen ....................... | 422/121 |
| 6,053,968 A | * | 4/2000 | Miller .......................... | 96/224 |
| 6,235,090 B1 | * | 5/2001 | Bernstein et al. .............. | 96/57 |
| 6,264,888 B1 | * | 7/2001 | Palestro et al. ............... | 422/24 |
| 6,497,840 B1 | * | 12/2002 | Palestro et al. ............... | 422/24 |
| 2002/0144601 A1 | * | 10/2002 | Palestro et al. ............... | 95/273 |

FOREIGN PATENT DOCUMENTS

| | | | |
|---|---|---|---|
| DE | 1908450 | * | 9/1970 |
| DE | 2732859 | * | 2/1979 |
| DE | 2817772 | * | 10/1979 |
| EP | 0 461 310 | * | 12/1991 |
| WO | 94/08633 | * | 4/1994 |
| WO | 98/38462 | * | 9/1998 |

OTHER PUBLICATIONS

References marked with X were cited in applicant's parent U.S. Appl. No. 10/182,915.*

* cited by examiner

Primary Examiner—Richard L. Chiesa
(74) Attorney, Agent, or Firm—Ohlandt, Greeley, Ruggiero & Perle, L.L.P.

(57) ABSTRACT

An air extraction and treatment unit is located above a source of contaminated air. The apparatus has a series of ultraviolet tubes for treating the decontaminated air. The unit is arranged such that in use substantially no direct or reflected ultraviolet light is visible from outside the unit. Furthermore even when a removable filter is removed, there is no direct line of sight to the ultra-violet source. The unit further has a first switch being disposed between a first filter and the unit. The first switch modulates the ultraviolet tubes between at least a first condition and a second condition.

19 Claims, 7 Drawing Sheets

AIR TREATMENT APPARATUS

CROSS REFERENCE TO RELATED APPLICATIONS

This application is a continuation-in-part of U.S. patent application Ser. No. 10/182,915, filed on Oct. 1, 2002 and International Application No. PCT/GB01/00456, filed on Feb. 5, 2001. This application claims priority of Great Britain Patent Application No. 0002679.9, filed on Feb. 4, 2000.

FIELD OF THE INVENTION

This invention relates to a safety apparatus for treating contaminated air such as is produced in commercial kitchens, e.g. to remove odors and the like therefrom.

BACKGROUND OF THE INVENTION

The usual way to treat air laden with grease and odors which is produced by a cooking appliance is to extract air from above the appliance to the outside by means of an extraction unit. The extraction unit is mounted above the appliance. This extraction unit is generally in the form of a hood and includes a number of filters and/or particle traps to trap grease and other particles in the air. Some sort of deodorizing means is also often included such as an activated carbon filter or a source of fragrant masking oil.

The problems with mechanical filters are that they tend to need regular replacement or cleaning and also that when laden with grease etc., they represent a significant fire hazard.

Proposals have been made to use ultra-violet light to decontaminate air in air extraction units of the type described above. In these arrangements ultra-violet tubes are provided above the air inlet behind the front wall of the unit. This front wall therefore hides the tubes from direct view. However since these units are fabricated from stainless steel, when the tubes are in operation light from them escapes through the air inlet and is reflected off the downwardly extending rear wall of the unit, thus making the light clearly visible.

The inventors have realized however that even reflected light from the UV tubes typically used in these applications is hazardous despite the previous tacit assumption to the contrary.

SUMMARY OF THE INVENTION

When viewed from a first aspect therefore the present invention provides an air extraction and treatment unit for mounting above a source of contaminated air. The unit has an air inlet through which the contaminated air is extracted in use, an air outlet through which decontaminated air is expelled in use, and an air treatment means disposed therebetween. The air treatment means has an ultraviolet light source. The unit is arranged such that in use substantially no direct or reflected ultraviolet light is visible from outside the unit.

Thus it will be seen that in accordance with the invention, the hazards of exposure even to reflected ultra-violet (UV) light are substantially avoided. This means that such units can safely be employed at the source of contaminated air e.g. at a cooking appliance in a commercial or industrial kitchen even though someone may need to work very close to the unit while using the appliance. A person working in the vicinity of the unit will not necessarily even know that it contains a potentially hazardous UV radiation source. In accordance with the invention no particular special precautions need be taken.

Air is typically moved through units of the type to which the invention applies by a remote fan downstream of the unit, e.g. just before the decontaminated air is exhausted to the atmosphere. Commonly a single such fan will serve several air extraction and treatment units.

The unit may be arranged just with suitably positioned walls to avoid the escape of light from the unit. This is relatively easy to achieve for most of the walls of the unit. Of course, however, the air inlet must be in fluid communication with the exterior of the unit and therefore particular precaution is necessary to avoid the potential escape of UV light from any angle, which might render it visible to a user. The region of the air inlet may therefore be defined with suitably positioned walls.

In preferred embodiments however a filter is disposed in the path of incoming air forming at least part of the barrier to light escaping. This filter is preferably arranged to remove relatively large particles, e.g. grease and/or fat, from the air passing through it.

In the most preferred embodiment the filter is of the type which forces air flow therethrough to change direction abruptly. This arrangement has been is found to be best for removing larger particles of fat and grease by means of a centrifuge effect without clogging the filter. Most preferably the filter is reusable and therefore requires at most periodic cleaning.

The filter may be permanently or semi-permanently fixed, i.e. with the intention that it is not removed by an ordinary user. Preferably though the filter is removable, e.g., for cleaning. As stated above, in preferred embodiments—the filter provides at least part of the barrier against the escape of UV light. It follows therefore that if it is removed there will no longer be such a barrier. The inventors have realized that whilst direct UV light of the sort used to deodorize air can be hazardous with only brief exposures, light reflected from stainless steel parts is hazardous only with longer exposures.

Thus where the unit comprises a removable filter providing at least part of the light barrier, the rest of the unit is preferably arranged such that even with the filter removed no direct UV light from the unit is visible, i.e. only reflected light is visible.

Such a feature is considered to be inventive in its own right. Viewed from a second aspect therefore, the invention provides an air extraction and treatment unit for mounting above a source of contaminated air. The unit has an air inlet through which the contaminated air is extracted use, an air outlet through which decontaminated air is expelled in use, a removable air filter disposed in the path of incoming air, and an air treatment means disposed downstream of the air filter with an ultra-violet source. When the air filter is removed there is no direct line of sight between the ultraviolet source and the outside.

Thus exposure to direct UV light can be avoided at the time of filter removal.

It will be appreciated that references herein to a removable filter cover at least both a filter which can be fully removed, e.g. for machine washing, and a filter which is removed from its normal operating position but is not fully detached from the rest of the unit, e.g. by hinging open for manual cleaning in situ.

It is further preferred that means are provided to reduce or interrupt the supply of power to the UV source in the event that such a filter is removed. Additionally or alternatively means are provided to interrupt or reduce the power in the event that any part of the unit is dismantled.

The means for interrupting or reducing the power may comprise a switch such as a micro-switch in the region of the removable filter or other removable part of the unit, but preferably comprises pressure sensing means which can sense the drop in pressure inside the unit if the filter or any other part is removed. This is beneficial since it means that the UV source can be switched off if any leak develops. Even if not associated with an intentionally removable part.

In the preferred arrangement in which there is both a power supply reduction or interruption when the filter is removed, and no direct line of sight between the UV source and the outside, if there is a delay or malfunction in the operation of the former safety feature, the latter provides an additional safety feature.

It is also a preferred feature of the present invention that a baffle is provided which is arranged to direct incoming air across the whole area covered by the UV light source or sources. In one convenient embodiment it is this baffle prevents direct light from the UV source escaping from the unit even when a removable filter is removed.

Downstream of the filter, there may be provided means to cause one or more further changes in the direction of air flow. This directional change provides an additional fat and grease removal effect. Such means may comprise the baffle mentioned above.

In a further embodiment of the present invention, there is proved an air purifier. The air purifier has a ventilation hood with a ventilation hood inlet, a ventilation outlet, and a ventilation hood plenum disposed therein. The air purifier has a ventilation duct having a ventilation duct inlet that is connected to the ventilation hood outlet, and further has a ventilation duct outlet. The air purifier has a fan for drawing contaminated air through the ventilation hood inlet into the ventilation hood plenum. The air purifier has an ultra violet radiation generating apparatus for generating ultra violet radiation. The ultra-violet radiation is incident on the contaminated air stream and generates ozone in the contaminated air stream. The ozone oxidizes contaminants in the contaminated air stream. The air purifier has a first filter being disposed at the ventilation hood inlet. The first filter blocks the ultra violet radiation.

In another embodiment of the present invention, there is provided an air purifier that has a ventilation hood with a ventilation hood inlet, a ventilation outlet, and a ventilation hood plenum disposed therein. The air purifier has a ventilation duct having a ventilation duct inlet being connected to the ventilation hood outlet and a ventilation duct outlet. The air purifier has a fan for drawing contaminated air through the ventilation hood inlet into the plenum and an ultra violet radiation generating apparatus having an illuminated state and a non-illuminated state. The ultra-violet radiation generating apparatus generates ultra violet radiation.

The ultra-violet radiation is incident on the contaminated air stream and generates ozone in the contaminated air stream. The ozone oxidizes contaminants in the contaminated air stream. The air purifier has a plurality of grease filters being disposed at the ventilation hood inlet in a plurality of slots. The plurality of grease filters block the ultra violet radiation. A first switch is between a first one of the plurality of grease filters and the ventilation hood. The first switch is in electrical communication with a power source. A second switch is disposed between a second one of the plurality of grease filters and the ventilation hood. The second switch is in electrical communication with the power source and the first switch. In an embodiment of the present invention, both the first switch and the second switch could sense a pressure change in the substantially same location in an extraction or canopy hood.

The first switch, the second switch and the power source are in electrical communication with the ultra violet radiation generating apparatus. Upon an occurrence that any of the grease filters are removed or an exhaust fans fails, the first switch and/or the second switch interrupts power from the power source to the ultra violet radiation generating apparatus to protect a user from exposure from ultra-violet rays emitted or reflected from the ultra violet radiation generating apparatus.

BRIEF DESCRIPTION OF THE DRAWINGS

Certain preferred embodiments of the present invention will now be described, by way of example only, with reference to the accompanying drawings in which.

DESCRIPTION OF THE PREFERRED EMBODIMENT

Figure 1:
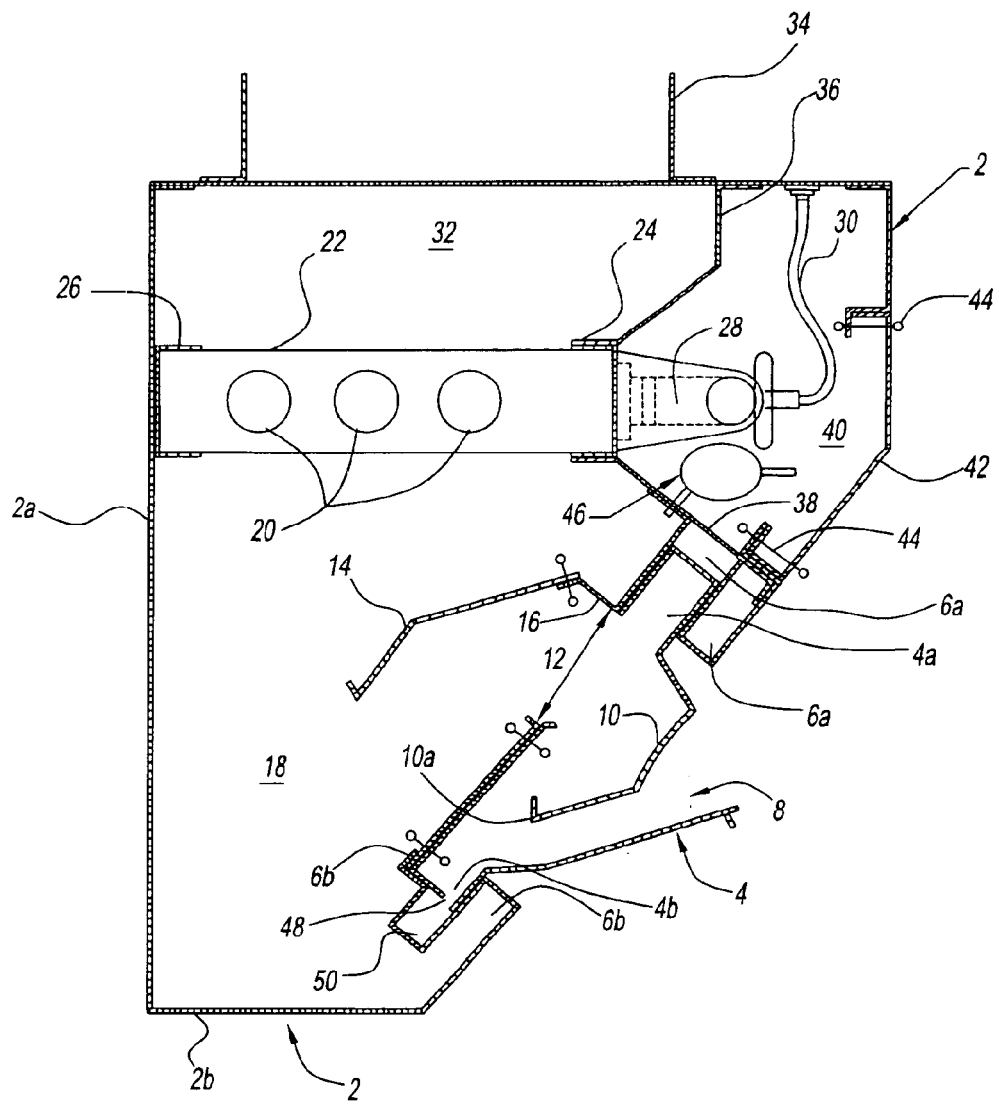
FIG. 1 is a cross-sectional view of an air extraction and treatment unit in accordance with the present invention.

Turning to FIG. 1, this shows a cross-section through an air extraction and treatment unit, which is installed above a cooker in a commercial kitchen (not shown). The unit is generally encased in a stainless steel housing 2, which is attached to a wall along its rear wall 2a. A grease filter 4 is arranged towards the front of the unit. The filter has respective upper and lower extensions 4a, 4b that are received in corresponding slots 6a, 6b formed in the unit housing. The grease filter 4 has an air inlet opening 8 and an internal baffle 10, which depends from the rear edge of the opening 8. It will be seen from FIG. 1 that when the grease filter 4 is installed in the position shown, it covers an opening 12 in the housing of the unit, which would otherwise be present.

Figure 1A:
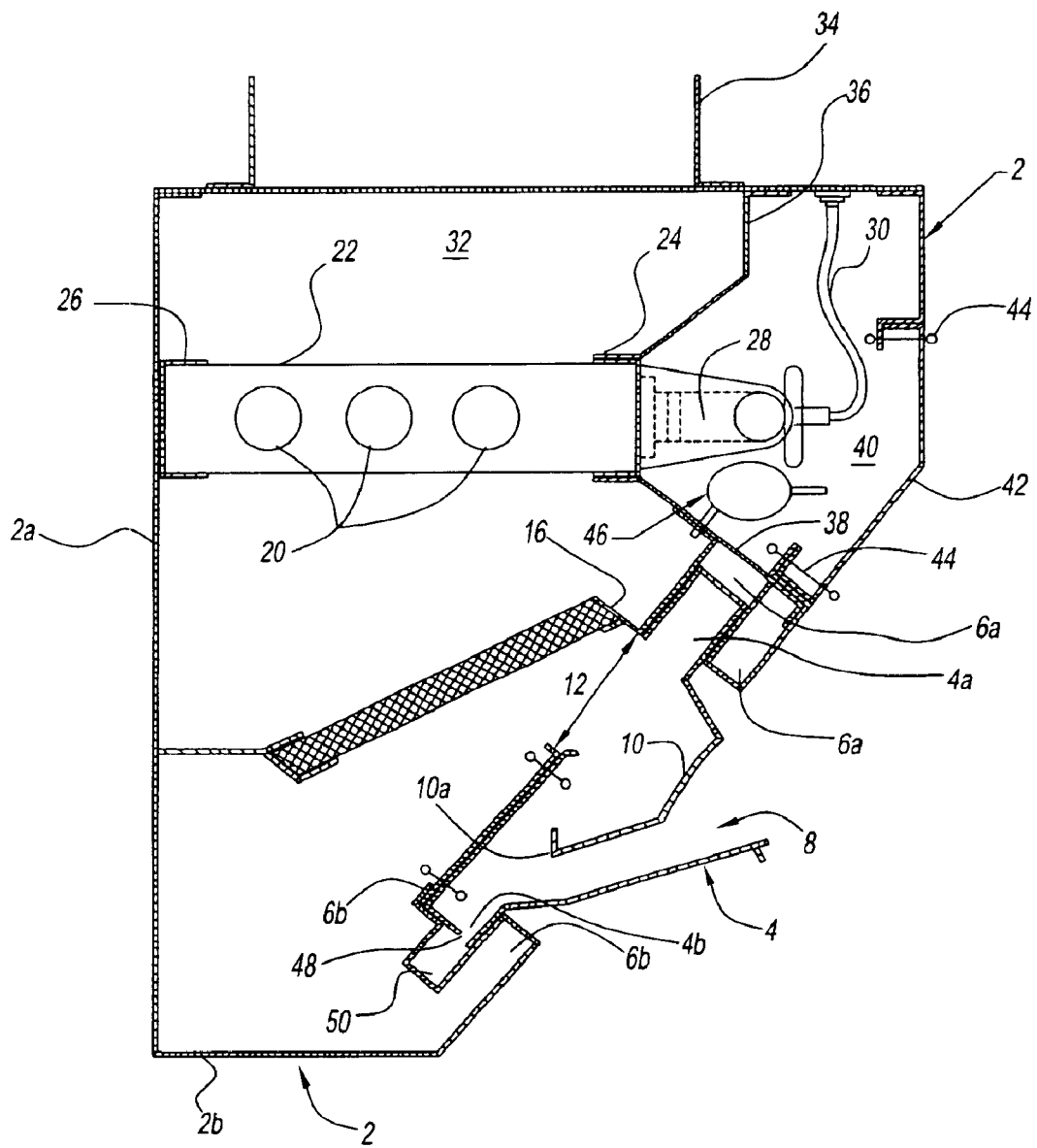
FIG. 1A is a cross-sectional view of an air extraction and treatment unit of FIG. 1 with an alternative baffle.

Between the opening 12 and the rear wall 2a of the housing there is defined a plenum 18. A baffle 14, which is fixed to a short extension 16 of the wall defining the opening 12, extends into the plenum 18. The baffle 14 is bent so as to direct air entering the plenum diagonally downwardly. In another exemplary embodiment of the present invention the baffle 14 may be a longitudinally shaped member having a thickness as shown in FIG. 1A, a filter HEPA filter, or a coalescer. One skilled in the art should appreciate that the baffle 14 may be any member that does not allow light to penetrate therethrough or reflect therefrom to potentially harm the eyes. At the top of the plenum 18 is an array of UV tubes 20 which are held in a cassette 22. The cassette 22 is slidably received in front and rear brackets 24, 26 respectively. A series of clips (not shown) provided to hold the cassette 22 in place. Electrical connection to the UV tubes 20 is made by means of a removable electrical connector 28 and electrical supply cable 30.

Above the UV cassette 22 is a further space 32, which communicates with an air outlet duct 34. The front of the space 32 is delimited by a wall 36 which, in conjunction with the forward portion of the UV cassette 22 and a similar wall 38 defining part of the lower plenum 18, defines a front access space 40 separated from the air flow in which the electrical connector 28 and supply cable 30 are housed. The front panel 42, which provides access to this space, is secured to the main housing 2 of the unit by means of a series of special screws 44 (shown only schematically). These screws have specially shaped heads in order to ensure that only qualified service personnel possessing the complementary tool are able to remove the panel 42 and therefore gain access to the UV cassette 22.

Finally, a pressure sensor 46 is disposed in the front access space 40 adjacent the upper slot 6a for receiving the grease filter 4. This pressure sensor 46 is electrically connected to a control device (not shown) for switching off the electrical supply to the UV cassette 22 in the event that a drop in pressure in the plenum 18 is detected. This will arise for example if the grease filter 4 is removed or if the front panel 42 is removed since the enclosed front access space 40 is not pressure-sealed from the plenum 18 or space 32 or in the event of an exhaust fan failure being located in the air outlet 34.

One skilled in the art will appreciate that the location of the pressure sensor 46 in plenum 18 is not limited to that location being shown in FIGS. 1 and 1A. The pressure sensor 46 can be located anywhere in the space 32 and it will still perform the same function. For example, the pressure sensor 46 could also be located anywhere in space 32 including above the cassette 22. One skilled in the art should further appreciate to facilitate maintenance concerns associated with the air extraction and treatment unit and to bypass opening the front panel 42, the pressure sensor 46 does not have to be physically located in either plenum 18 or space 32 at all. The pressure sensor 46 can be alternatively located anywhere outside of the housing 2, and pressure detection in either plenum 18 or space 32 can be done by usage of a tube (not shown) between a remote pressure sensor and a measurement point being located in either the plenum 18, the space 32 or a combination thereof. One skilled in the art should appreciate the cost benefit to run tubing in the plenum 18 or space 32 or both is less expensive than to run, for example electrical wiring.

Figure 2:
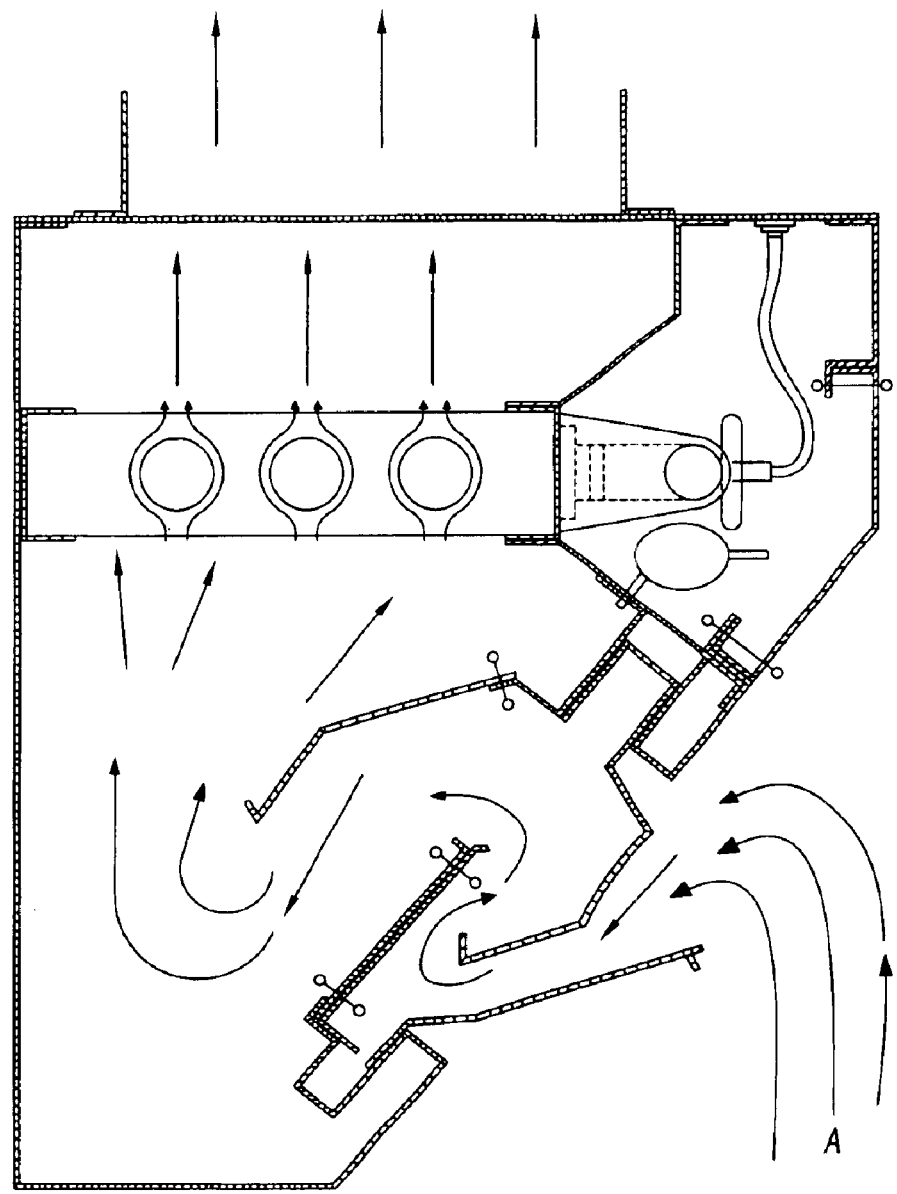
FIG. 2 is the same view of FIG. 1 except for the removal of reference numerals for clarity and the addition of air flow arrows.

Operation of the unit will now be described. Reference is made to FIGS. 1, 1A, and 2, which is the same as FIG. 1 but with the reference numerals omitted for clarity and the pattern of air flow marked thereon for illustration purposes only.

A fan (not shown) downstream of and in fluid communication with the air outlet duct 34 creates a large negative pressure in the unit, which draws air through it. Air emanating from the cooker and laden with grease, fat and other organic substances is therefore drawn upwardly and through the air inlet opening 12 in the grease filter 4. The air is forced to flow around the internal baffle 10 in the grease filter and in particular around the sharp angled bend 10a at the lower end thereof. This sharp change of direction causes larger particles of grease as fat to be thrown out of the air stream and into the recess 4b in the grease filter for collection and subsequent disposal thereof.

The collected grease/fat will tend to remain molten due to the relatively high temperature of the walls of the grease filter and therefore drains through the discharge hole 48 into a recess 50 in the main housing. Although not visible from the Figures, the recess 50 is inclined in a longitudinal direction so that the molten grease and fat collects in a designated sump and may be easily removed. Again, the relatively high temperature of the metal walls of the recess 50 keeps the grease/fat molten.

Once the air has passed around the distal end 10a of the internal baffle 10, it passes back up the rear half of the grease filter 4 and exits through the opening 12 into the plenum 18. The baffle 14, which is disposed in this plenum, directs the air diagonally downwardly towards the bottom rear corner of the plenum. However, the negative pressure induced by the fan draws the air generally upwardly and therefore causes it to curl around the distal edge of the baffle 14 and towards the UV tubes 20 as shown in FIG. 2. The air is drawn over the surfaces of the UV tubes 20.

The UV light causes ozone to be generated from oxygen present in the air and the ozone proceeds to oxidize the organic contaminants present in the air. The UV radiation also breaks down the larger organic substances through the process of photolysis. These processes are highly effective at removing odors from the air. Once odors and other organic substances have been removed, the air passes up into the space 32 and then through the outlet duct 34 from which it may be exhausted safely to the atmosphere.

It may clearly be seen from FIGS. 1 and 2 that not only is it impossible to trace a direct light path from any of the UV tubes to the region outside the unit, nor can any such path be traced for light reflected from the rear wall 2a, lower wall 2b, or indeed any other part of the apparatus.

Figure 3:
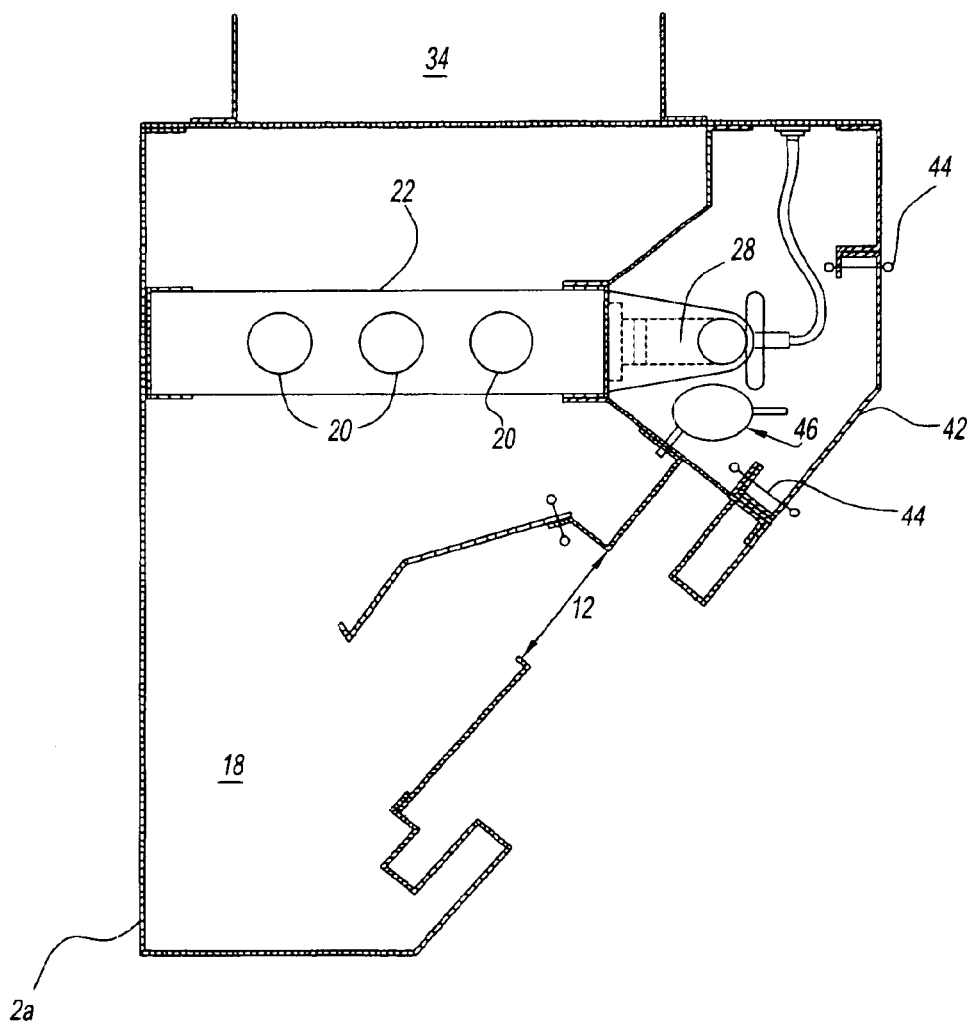
FIG. 3 is a cross-sectional view of the same unit as in FIGS. 1 and 2 with the filter removed.

Turning now to FIG. 3, the same air extraction and treatment unit is shown as in FIGS. 1 and 2, except that this time the grease filter 4 has been removed. If this is done while the unit is still operational, the pressure sensor 46 will sense the resultant drop in pressure and cut the supply of electrical power to the UV tubes 20. However, as may clearly be seen, even if the power to the UV tubes 20 were not to be cut for any reason, the internal baffle 14, the filter and/or coalescer prevents any direct line of sight between the opening 12 and the UV tubes 20, although it is now possible through a small angle to see the back wall 2a of the plenum 18 and therefore any light reflected from this. However, a warning sticker (not shown) warns the user to switch off the unit if this area should become visible. With the grease filter 4 or longitudinal member of FIG. 1A removed, the user may gain access to the plenum 18 to clean it periodically. Since the result of the UV oxidation process is fine, dry dust, cleaning is relatively straightforward.

In order to clean or replace any of the UV tubes, an authorized service person possessing the right tool must use it to undo the special screws 44 and remove the front panel 42. The electrical connector 28 may then be removed from the UV cassette 20 and the clips (not shown) retaining the cassette 22 in place may be undone. This allows the cassette 22 to be slid out horizontally from the brackets 24, 26 to allow the tubes to be cleaned with a damp cloth and/or replaced.

Figure 4:
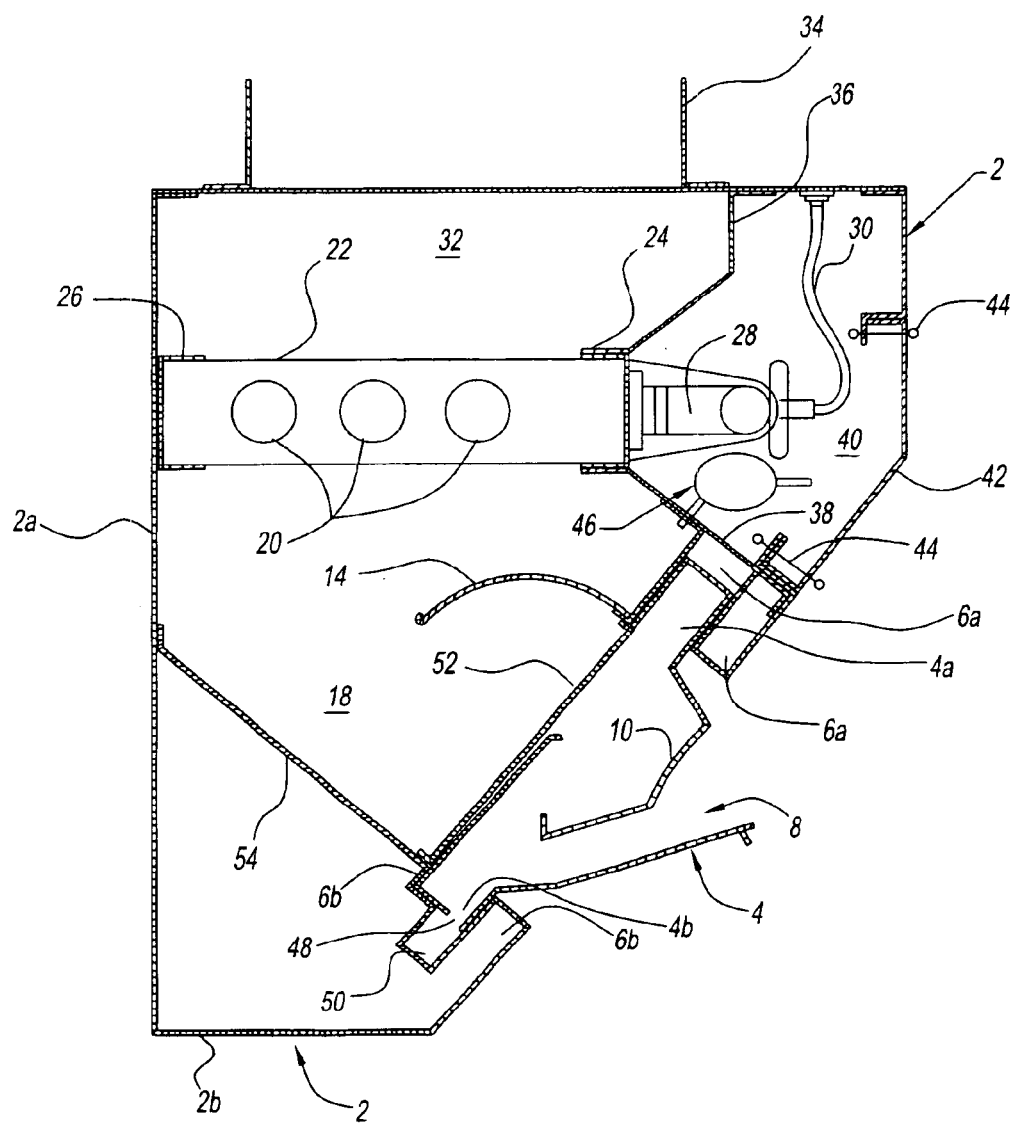
FIG. 4 is a cross-sectional view of a second embodiment of the invention.

A second, preferred embodiment of the invention is shown in the cross-sectional view of FIG. 4. This embodiment is substantially similar to the first and thus only the difference therebetween will be mentioned.

The first difference is that there is no inclined wall extending from the rear of the lower slot 6b to form the opening 12 as there is in FIGS. 1 to 3. Instead, a series of vertical spacers 52 is provided at longitudinally spaced intervals along the apparatus and which extend between the upper and lower slots 6a and 6b. The longitudinal gaps between the spacers 52 are slightly shorter than the width of individual filter units 4 such that the filters 4 overlap the spacers 52 at the edges thereof. The cross-section in FIG. 4 is taken at one such point. This overlapping arrangement further ensures that no direct or reflected UV light from the UV tubes 20 is able to escape from the front of the apparatus.

Secondly, a sloping base wall 54 is included, extending from the rear of the plenum 2a to the recess or alternatively a grease collection channel 50. This sloping base wall 54 serves to direct any remaining grease in the chamber 18 into the grease collection channel 50.

Thirdly, the upper baffle 14, or alternatively the coalescer or filter is curved in profile. Furthermore it is manufactured in longitudinal sections to facilitate removal, e.g., for cleaning etc.

Figure 5:
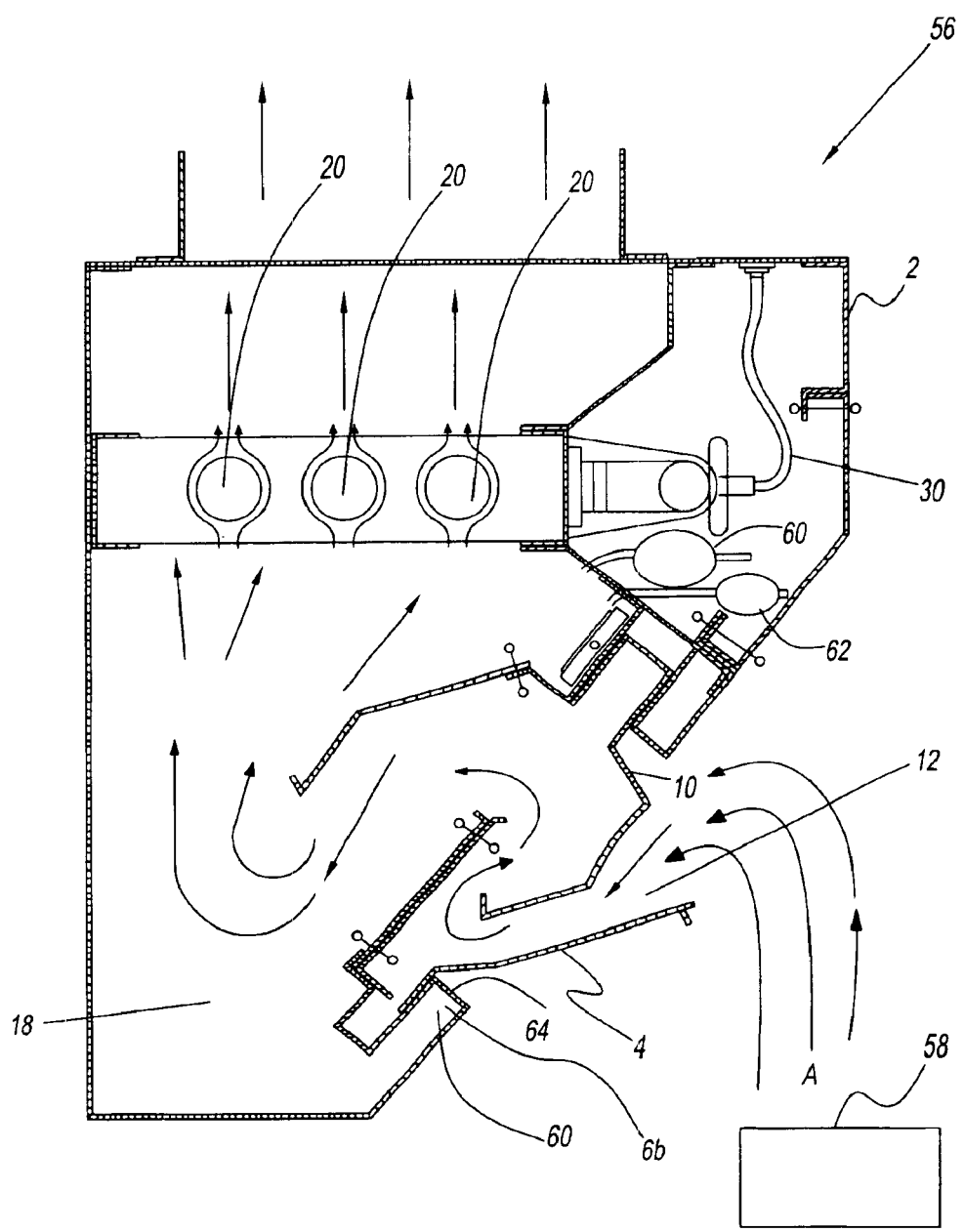
FIG. 5 is another cross-sectional view of another embodiment of the air extraction and treatment unit.

In another embodiment of the present invention, referring to FIG. 5, there is provided an air purifier generally designated as reference numeral 56 being disposed above a cooking appliance 58. One skilled in the art should appreciate that the present invention may be incorporated in a retrofit manner to existing ventilation units, ventilation hoods, ventilation ducts, air purifier and any other non-cooking appliance air purification devices known in the art.

Air purifier 56 has the stainless steel housing 2 that has one or more grease filters 4 being connected to the inlet air opening 12. The air purifier 56 also has the one or more UV tubes 20 disposed in the cassette 22 being electrically coupled to the supply cable 30.

The air purifier 56 also has a first pressure switch 60 and a second pressure switch 62. However, one skilled in the art should appreciate that the first and second pressure switch 60, 62 could be disposed in any suitable location in close relation to the grease filters 4. The location is sufficient such that upon removal of the grease filter 4, the first pressure switch 60 and the second pressure switch 62 are actuated.

The first and second pressure switches are in electrical communication with the UV tubes 20 and also coupled to a power source (not shown) by the supply cable 30. Upon removal of the grease filter 4, the first and/or second pressure switch 60, 62 are actuated. Upon actuation of the first and second pressure switches 60, 62 the power supplied from the power source by the supply cable 30 to the UV tubes 20 is interrupted for safety purposes. This operation improves the safety of the air purifier 56 and further prevents the UV tubes 20 from exposing the user with ultra-violet radiation.

Although, shown as the air purifier 56 using ultra-violet light being disposed over a cooking appliance, one skilled in the art should appreciate that the present disclosure may be used in connection with any other air purifier technologies known in the art for removing contaminants from air or fluid.

Preferably, the air purifier 56 has one or more UV tubes 20 that are preferably ultra-violet light tubes that emit energetic photons and emit ultra-violet radiation having a wavelength less than about 254 nanometers. In another embodiment of the present invention, the one or more UV tubes 20 emit radiation having a wavelength of about a 185 nm wavelength. In another preferred embodiment, the one or more UV tubes 20 have a wavelength of about 185 through 254 nm. The one or more UV tubes 20 are preferably between the plenum 18 and the space 32 and irradiate the contaminated air stream passing incident therethrough for treating the contaminated air stream.

One skilled in the art should appreciate that the one or more UV tubes 20 may emit radiation having any wavelength suitable for producing ozone. One skilled in the art should appreciate that any suitable number of UV tubes 20 are intended to be used to impart oxidation benefits to the contaminated air stream passing through the plenum 18. In another embodiment, a number of UV tubes 20 may have different wavelengths.

Disposed in a substantially rear side of each of the one or more grease filters 4 adjacent the slot 6b is the first pressure switch 60. The first pressure switch 60 is preferably a pressure switch being in electrical communication to the one or more ultra-violet tubes 20 and the power source (not shown). In the unlikely event that the one or more grease filters 4 are removed, power from power source (not shown) to the one or more ultra-violet tubes 20 will be interrupted. Accordingly, an illumination of the one or more ultra-violet tubes 20 is modulated.

Referring again to FIG. 5, the second pressure switch 62 may also be located in a second location different than a location of the first pressure switch 60 or in the same location as the first pressure switch. In another embodiment, the second pressure switch 62 may be placed between the stainless steel housing 2 and the internal baffle 10 and in electric communication with the power supply. In this manner, somehow, if the internal baffle 10 is removed the second pressure switch 62 will be actuated. This actuation will modulate the ultra violet tubes 20. In another preferred embodiment, the second pressure switch 62 is disposed between a second grease filter (not shown) and the housing 2. The first and second pressure switches 60, 62 are preferably mechanical pressure switches. However, one skilled in the art should appreciate that the first and second pressure switches may be any air pressure switches, mechanical pressure switches, or mechanical pressure sensors. The first and the second pressure switches 60, 62 may have two states, open or closed, or more states and can alternatively generate various signals like current, voltage, resistance, or closure of contacts as a function of a monitored input to modulate the operation of UV tubes 20.

Figure 6:
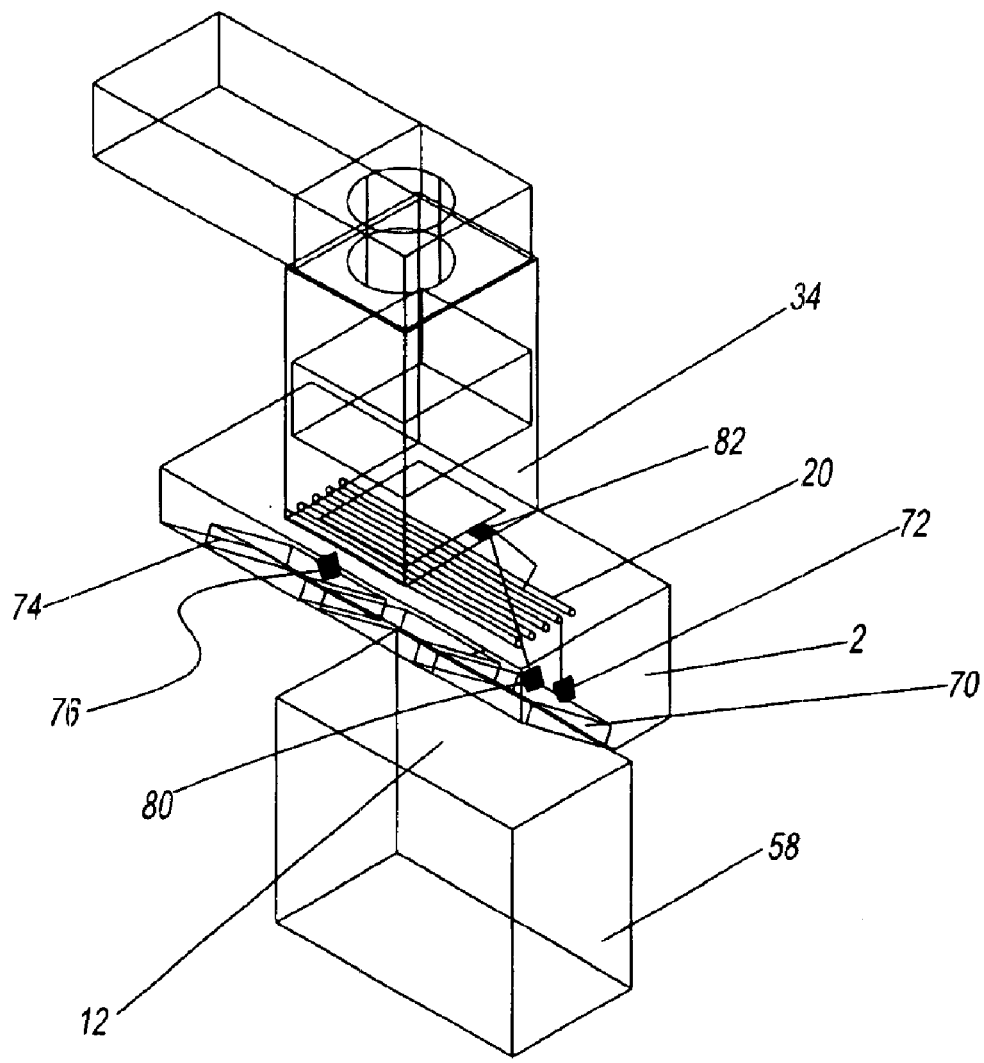
FIG. 6 is a perspective cross-sectional view of another embodiment of an air purifier.

Referring to FIG. 6, in another exemplary embodiment of the present invention, a first grease filter 70 has a first switch 72 disposed in a rear side therein and a second grease filter 74 has a second switch 76 also disposed in a rear side therein. The first switch 72 and the second switch 76 are electrically coupled in parallel or series to one or more UV tubes 20 and the power source (not shown). In this manner, upon the condition that either grease filter 70, 74 is removed then the corresponding switch disposed in a rear side of the grease filters 70, 74 is actuated. This actuation of the first and/or the second switches 72,76 modulate power from the power source (not shown) to the UV tubes 20.

Although, illustrated as being disposed in a rear side of the one or more grease filters 70, 74 each switch 72,76 is preferably disposed at a location defined as an intersection between the respective grease filter and the housing 2. This location is suitable such that upon removal of the grease filter 4, the respective switch 72, 76 will open/close for modulating power to the UV tubes 20. One skilled in the art will appreciate that safety of the unit is increased because if the first pressure switch or second pressure switch 72, 76 fail or is otherwise rendered inoperably the level of safety of the overall unit is maintained. This is beneficial especially because often the kitchen staff will not be aware that they are being exposed due to the invisible nature of the ultraviolet light at this wavelength. This actuation of the first and/or the second switches 72, 76 modulate power from the power source (not shown) to the UV tubes 20.

Switches 72, 76 each or both may be a pressure switch, a spring-biased switch, a manual switch, a proximity switch, a magnetic switch, an optical switch or any other switch mechanism known in the art, or a combination thereof. Switches 72, 76 are each preferable hermetically sealed, and can operate at a high temperature while being compact, lightweight, with accurate repeatability and long life.

Preferably, each switch 72, 76 is sealed to prevent damage from the contaminants, effluent, grease and oil in the contaminated air stream that traverses near the respective switch to enter the ventilation duct. Each switch 72, 76 preferably is suitable to be resistant to a high temperature given the immediate proximity to the cooking appliance 58 and the contaminated air stream. Alternatively, each switch 72,76 may also be a sealed switch, a pushbutton switch, a key switch having an indicators for manual operation, a high reliability snap-action temperature switch for temperature control, a sealed rocker switch, or any other switch known in the art or known in the future.

In another exemplary alternative embodiment of the present invention, air purifier 56 may also further comprise a sensor 80. Sensor 80 is preferably disposed at the intersection defined between the grease filter 4 and the opening 12. Sensor 80 preferably emits signals in response to an occurrence of the removal of the grease filter 4. The sensor 80 may arranged with a second pressure sensor or a number of sensors and further be electrically connected to a suitable analog or digital controller 82 such that the controller 82 receives the output signal of the sensor 80.

Controller 82 may also be a suitable electronic circuit for controlling the power supplied to the UV tubes 20 by the power source as a function of the output signal of the sensor 80. The controller 82 may also further have a memory 84 having a suitable algorithm for modulating of the ultra-violet tubes 20. The electronic circuit is coupled to the controller 82 for modulating an operating condition of the UV tubes 20.

In this manner upon removal of the one or more grease filters 4, or failure of the exhaust fan, the sensor 80 emits one or more signals responsive to the removal of the one or more grease filters 4 to the controller 82. The controller 82 in response thereto modulates power from the power source in a pre-selected manner to ultra-violet tubes 20 to protect the user. The output signal of the sensor 80 is then transmitted to preferably a microprocessor, preferably a digital signal processing microprocessor that modulates the UV tubes 20, preferably suspending power to the UV tubes.

Modulating the one or more UV tubes 20 is preferably shown as terminating power from the power source (not shown) to the UV tubes 20, one is skilled in the art should appreciate that modulation may include other modes of operation. These modes include, but are not limited to, reducing electrical power to the ultra-violet tubes 20, rotating the ultra-violet tubes away from a user, rotating the cassette 22, or manipulating a shielding member (not shown) to replace the blocking aspects of grease filter 4 and shield the user from the ultra-violet light.

This manipulation may include moving an intermediate member (not shown) between the user and the one or more ultra-violet tubes 20 and/or the cassette 22. In an embodiment of the present invention, upon removal of the grease filter 4, the UV tubes 20 are modulated by switching the UV tubes from illuminated to non-illuminated.

In another embodiment of the present invention, for example where three grease filters are used, a first, a second and a third pressure switch are all coupled in parallel or series to the one or more UV tubes 20. Upon the occurrence that any grease filter is removed, the corresponding pressure switch operates to toggle all ultra-violet tubes 20 from the illuminated state to the non-illuminated state. In this manner, upon the removal of the one or more grease filters, the air purifier 56 modulates the power to the UV tubes 20 to avoid exposing a user by ultra-violet radiation.

The present invention having been thus described with particular reference to the preferred forms thereof, it will be obvious that various changes and modifications may be made therein without departing from the spirit and scope of the present invention.

What is claimed is:

1. An air purifier comprising:
    a ventilation hood with a ventilation hood plenum disposed therein;
    a ventilation duct connected to said ventilation hood;
    a fan for drawing contaminated air through said ventilation hood into said ventilation hood plenum;
    an ultra violet radiation generating apparatus which generates ultra violet radiation that is incident on a contaminated air stream traversing through said ventilation hood plenum, said ultra-violet radiation generating apparatus generating ozone for oxidizing a plurality of contaminants in said contaminated air stream;
    a first member being disposed at an inlet of said ventilation hood, wherein said first member blocks said ultra violet radiation from exposing an individual in proximity to the air purifier; and
    a first switch being disposed between said first member and the air purifier, said first switch modulating said ultra violet radiation generating apparatus between at least a first condition and a second condition upon removal of said first member.

2. The air purifier of claim 1, further comprising a second switch, said second switch being disposed between a second member and the air purifier, wherein said first switch and/or said second switch modulates said ultra violet radiation generating apparatus between said first condition and said second condition upon an occurrence being selected from the group consisting of: a removal of said first member, a removal of said second member, a removal of both said first member and said second member, a failure of an exhaust fan, and any combinations thereof.

3. The air purifier of claim 1, wherein said first member is a filter.

4. The air purifier of claim 1, wherein said first condition is an illuminated state of said ultra violet radiation generating apparatus and said second condition is a non-illuminated state of said ultra-violet generating apparatus.

5. The air purifier of claim 2, wherein said second condition is selected from the group consisting of: reducing electrical power to said ultra violet radiation generating apparatus, rotating said ultra violet radiation generating apparatus away from a user, rotating a cassette having said ultra violet radiation generating apparatus away from said user, manipulating a shielding member between said ultra violet radiation generating apparatus and said user, and any combinations thereof.

6. The air purifier of claim 1, wherein said first switch is hermetically sealed.

7. The air purifier of claim 1, wherein said first member has a first side and a second side, said first switch being disposed at said second side between said ventilation hood and said first member.

8. The air purifier of claim 1, wherein said first switch is in electrical communication with a controller, said controller modulating said ultra-violet radiation generating apparatus from said first condition to said second condition.

9. The air purifier of claim 1, wherein said first switch modulating said ultra violet radiation generating apparatus between at least a first condition and a second condition is disposed in a retrofit apparatus for an existing ventilation systems.

10. The air purifier of claim 1, wherein said first switch is selected from the group consisting of: a pressure switch, a spring-biased switch, a push button switch, an optical switch, a proximity switch, a magnetic switch, a key switch, a snap action switch, a temperature switch, a rocker switch, and any combinations thereof.

11. The air purifier of claim 2, wherein said second switch is selected from the group consisting of: a pressure switch, a spring-biased switch, a push button switch, an optical switch, a proximity switch, a magnetic switch, a key switch, a snap action switch, a temperature switch, a rocker switch, and any combinations thereof.

12. The air purifier of claim 8, wherein said controller is a digital signal processor having program instructions, said program instructions and said controller operable to modulate said ultra-violet radiation generating apparatus.

13. The air purifier of claim 1, wherein said first switch is resistant to heat being generated from a cooking appliance.

14. The air purifier of claim 1, further comprising a sensor, said sensor monitoring an operability condition of the air purifier, said sensor outputting a signal in response to a condition of the air purifier to a controller, said controller modulating said ultra-violet radiation generating apparatus from said first condition to said second condition.

15. The air purifier of claim 1, further comprising a second switch being disposed between a second member and the air purifier, said second switch being in electrical communication with said first switch, said ultra violet radiation generating apparatus, and a power supply, and wherein said first switch is in electrical communication with said second switch, said ultra violet radiation generating apparatus, and said power supply, wherein upon an occurrence that said first switch is toggled, said ultra violet radiation generating apparatus is rendered non-illuminated.

16. The air purifier of claim 15, wherein upon an occurrence that said second switch is toggled, said ultra violet radiation generating apparatus is rendered non-illuminated.

17. The air purifier of claim 1, wherein said first member is selected from the group consisting of: a grease filter, a filter, a HEPA filter, a coalescer, a first longitudinal member, a baffle, a baffling arrangement and any combinations thereof.

18. An air purifier comprising:
a ventilation hood having a ventilation hood inlet, a ventilation outlet, and a ventilation hood plenum disposed therein;
a ventilation duct having a ventilation duct inlet being connected to said ventilation hood outlet and a ventilation duct outlet;
a fan for drawing contaminated air through said ventilation hood inlet into said plenum;
an ultra violet radiation generating apparatus having an illuminated state and a non-illuminated state which generates ultra violet radiation that is incident on said contaminated air stream, said ultra violet radiation generating apparatus generating ozone in said contaminated air stream for oxidizing contaminants in said contaminated air stream;
a plurality of grease filters being disposed at said ventilation hood inlet in a plurality of slots, said plurality of grease filters blocking said ultra violet radiation;
a first switch being disposed between a first one of said plurality of grease filters and said ventilation hood, said first switch being in electrical communication with a power source;
a second switch being disposed between a second one of said plurality of grease filters and said ventilation hood, said second switch being in electrical communication with said power source and said first switch;
said first switch, said second switch and said power source being in electrical communication with said ultra violet radiation generating apparatus, wherein upon an occurrence that any of said plurality of grease filters is removed, said first switch and/or said second switch interrupts power from said power source to said ultra violet radiation generating apparatus to protect a user from exposure from said ultra-violet radiation being emitted or being reflected from said ultra violet radiation generating apparatus.

19. The air purifier of claim 18, further comprising a baffle arrangement, wherein said baffle arrangement blocks said ultra violet radiation, and wherein said baffle arrangement is disposed at said ventilation hood inlet, said baffle arrangement taking a contaminated air stream around a path, said path being substantially U-shaped for removing an amount of contaminants from said contaminated air stream.

* * * * *